(12) United States Patent
Stoll

(10) Patent No.: US 8,177,553 B2
(45) Date of Patent: May 15, 2012

(54) DENTAL STRIP

(76) Inventor: Walter Stoll, Toledo, OH (US)

( * ) Notice: Subject to any disclaimer, the term of this patent is extended or adjusted under 35 U.S.C. 154(b) by 18 days.

(21) Appl. No.: 11/493,954

(22) Filed: Jul. 27, 2006

(65) Prior Publication Data

US 2007/0148613 A1  Jun. 28, 2007

Related U.S. Application Data

(60) Provisional application No. 60/753,330, filed on Dec. 22, 2005.

(51) Int. Cl.
*A61C 5/04* (2006.01)

(52) U.S. Cl. ............... 433/39; 433/149; 132/329

(58) Field of Classification Search ............ 433/39, 433/215, 226, 40, 149, 148; 132/321, 329, 132/322–328; 33/513, 514
See application file for complete search history.

(56) References Cited

U.S. PATENT DOCUMENTS

| | | | |
|---|---|---|---|
| 3,108,377 A | 10/1963 | Meyer | |
| 3,795,052 A | 3/1974 | Mowery | |
| 4,211,330 A * | 7/1980 | Strock | 206/581 |
| 4,688,778 A * | 8/1987 | Woltron | 267/148 |
| 4,786,033 A * | 11/1988 | Kofler | 267/47 |
| 4,975,053 A * | 12/1990 | Hofsess | 433/25 |
| 5,040,981 A * | 8/1991 | Oliva | 433/141 |
| 5,330,353 A * | 7/1994 | Wavrin | 433/39 |
| 5,342,194 A * | 8/1994 | Feldman | 433/39 |
| 5,505,618 A * | 4/1996 | Summer | 433/148 |
| 5,620,322 A * | 4/1997 | Lococo | 433/39 |
| 6,350,122 B1 * | 2/2002 | Meyer | 433/39 |
| 6,619,956 B1 | 9/2003 | Weir | |
| 2005/0221255 A1 * | 10/2005 | Haraden et al. | 433/39 |

* cited by examiner

*Primary Examiner* — Todd Manahan
*Assistant Examiner* — Michael R Ballinger
(74) *Attorney, Agent, or Firm* — MacMillan, Sobanski & Todd, LLC

(57) ABSTRACT

An elongated flexible dental strip includes front and rear surfaces defining a thickness therebetween. The strip also includes first and second edges defining a lateral width therebetween. A first portion of the strip further is spaced from a second portion along the length of the strip, wherein the thickness of the first portion is different from the thickness of the second portion. The strip has a constant thickness across a lateral width defined between the first and second edges.

3 Claims, 6 Drawing Sheets

US 8,177,553 B2

DENTAL STRIP

CROSS REFERENCE TO RELATED APPLICATIONS

This application claims the benefit of U.S. Provisional Application No. 60/753,330 filed Dec. 22, 2005.

BACKGROUND OF THE INVENTION

This invention relates in general to dental products, and in particular to a dental matrix strip.

Dental strips, commonly referred to as matrix strips, are relatively small thin elongated plastic strips used in various dental procedures. Generally, the strips are used to isolate or shield the sides of adjacent teeth from one another. One known dental strip has a thin long rectangular shape. The strip is less than 1.0 mm in thickness and has a width of less than about 10 mm and a length of about 10 cm. The strip has a constant rectangular cross-sectional shape throughout the length of the strip. It is known to use such a strip to assist in filling an interproximal cavity, i.e., a cavity that develops on the side of a tooth. The strip is inserted between adjacent teeth and frictionally held in place therebetween. The strip helps retain the filling material within the prepared cavity during the curing process. The strip may be used to form or shape the filling material. The strip is physically placed over the filling material and manually manipulated to shape the filling material to a desired shape. The strip may also be used such that filling material used on one tooth will not inadvertently be placed on an adjacent tooth. Often times, the strips cannot simply be secured between the teeth due to the gap between the teeth. In this situation, a separate small wooden wedge is also inserted between the teeth against the strip to bridge the gap between the two teeth to secure the strip in place. Although the use of a wedge may retain the strip in place, the wedging force needed to retain the strip often causes irritation leading to undesirable bleeding of the gums of the mouth.

BRIEF SUMMARY OF THE INVENTION

This invention relates to a dental strip for use in dental procedures, such as to isolate the sides of adjacent teeth or to shape a filling material being applied onto a tooth. The flexible dental strip defines a length and includes front and rear surfaces defining a thickness therebetween. The strip also includes first and second edges defining a lateral width therebetween. A first portion of the strip further is spaced from a second portion along the length of the strip, wherein the thickness of the first portion is different from the thickness of the second portion. The strip has a constant thickness across a lateral width defined between the first and second edges.

Various objects and advantages of this invention will become apparent to those skilled in the art from the following detailed description of the preferred embodiment, when read in light of the accompanying drawings.

DETAILED DESCRIPTION OF THE INVENTION

In the following description of the invention, certain terminology will be used for the purpose of reference only, and is not intended to be limiting. Terms such as "inward" and "outward" refer to directions toward and away from, respectively, the geometric center of the component described. Terms such as "outer", "inner", "length", "width", "thickness", "front", "rear", "side", "top", "bottom", "horizontal", and "vertical" describe the orientation of portions of the component within a consistent but arbitrary frame of reference which is made clear by reference to the text and the associated drawings describing the component under discussion. Such terminology will include the words specifically mentioned above, derivatives thereof, and words of similar import.

Figure 1:
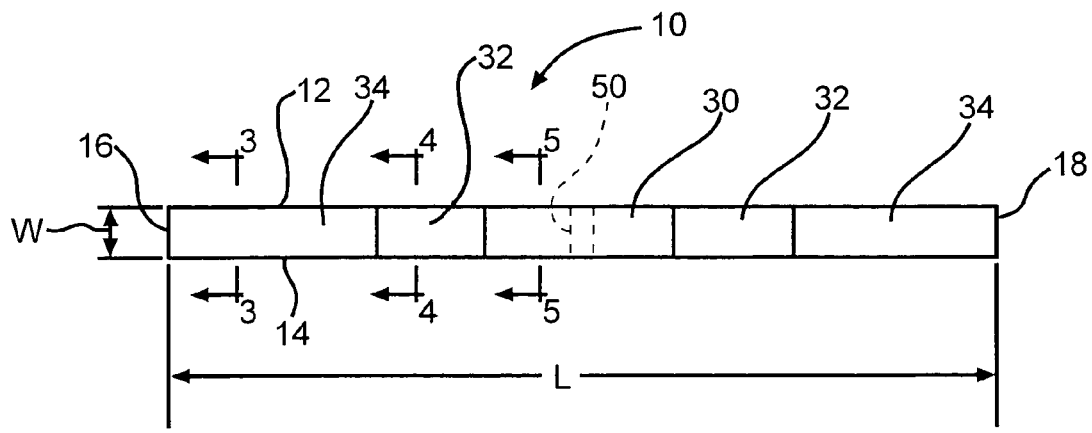
FIG. 1 is a plan view of a first embodiment of a dental strip, in accordance with the present invention.

Referring now to the drawings, there is illustrated in FIG. 1 a dental strip, indicated generally at 10. As will be explained in detail below, the strip 10 may be used in dental procedures for isolating or shielding the sides of adjacent teeth from one another. The strip 10 is inserted between the sides of adjacent teeth and frictionally held in place therebetween.

The strip 10 is preferably made of a flexible material, such as plastic, such that it is easily manipulated within and exterior of a patient's mouth. The strip 10 may also be transparent so that the dentist may see through the strip 10 during dental procedures. Another advantage of the strip being transparent is that light may be transmitted therethrough for light curing resin composites.

Figure 2:
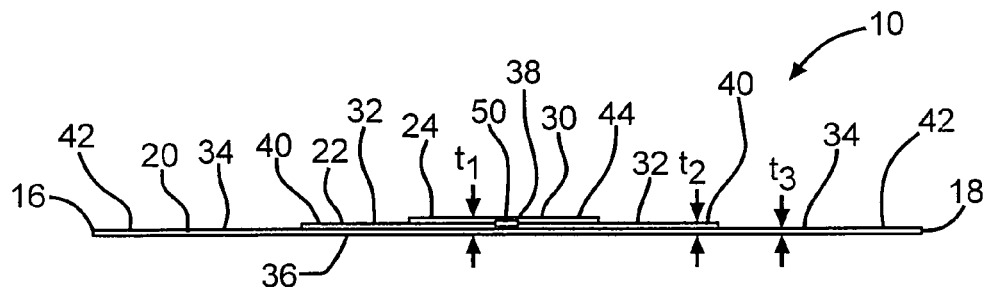
FIG. 2 is side elevational view of the strip of FIG. 1.

The strip 10 defines a lateral width W between edges 12 and 14. The strip 10 further defines a longitudinal length L between ends 16 and 18. Preferably, the width W of the strip 10 remains constant along the length of the strip 10, as best shown in FIG. 1. However, it should be understood that the width W need not remain constant along the length. As best shown in FIG. 2, the strip 10 includes various thicknesses (or heights) along the length thereof, the reason for which will be explained below.

As best shown in FIG. 2, the strip 10 generally includes three layers; a base layer 20, an intermediate layer 22, and an outer layer 24. The intermediate layer 22 is disposed between the base layer 20 and the outer layer 24. In the embodiment shown, the layers are separate strips laminated together to form the strip 10. The separate layers 20, 22, and 24 may be laminated together by any suitable manner, such as by an adhesive, heat sealing, ultrasonic welding, or other welding techniques. Alternatively, the layers 20, 22, and 24 may be subjected to heat to melt adjacent surfaces, thereby laminating the layers 20, 22, and 24 together. It should be understood that the strip 10 could be formed from a single piece or element, such as an extruded sheet, while still maintaining the contour of the illustrated strip 10 with the separate three layers 20, 22, and 24.

The layers 20, 22, and 24 are oriented and sized such that at least a portion of each of the layers 20, 22, and 24 are exposed. This arrangement provides the benefit of having various portions of the strip 10 with different thicknesses. In the embodiment shown, the strip 10 has a central portion 30, a pair of intermediate portions 32, and a pair of end portions 34. Each of the intermediate portions 32 are disposed between a respective end portion 34 and the central portion 30. The central portion 30 has a thickness $t_1$ defined between a generally planar rear surface 36 and a generally planar surface 38. Each intermediate portion 32 has a thickness $t_2$ defined between the rear surface 36 and a generally planar surface 40. Each end portion 34 has a thickness $t_3$ defined between the rear surface 36 and a generally planar surface 42. The surfaces 38, 40, and 42 generally define a stepped front surface 44. Thus, the surfaces 38, 40, and 42 are spaced from one another in a direction perpendicular to the planar surfaces 38, 40, and 42. The lengths and widths of the central portion 30, the intermediate portion 32, and the end portions 34 can be any desired size.

It should be understood that the thicknesses of the illustrated strip 10, as well as the other embodiments of dental strips herein, are exaggerated dimensionally, especially in thickness, for clarity purposes. Of course, the strip 10 (and any embodiments of the strips as described herein) can have any suitable thicknesses to accomplish their intended use, as described herein.

The strip 10 may also include indicia 50 printed thereon for preferably locating the center of the length of the strip 10. The indicia 50 provides for a visual indication to assist the user in folding or cutting the strip 10 in half, the reason for which will be explained below. The indicia 50 can be any marking such as a score line, an embossing, or an imprinted mark. The indicia 50 can be formed on the front surface 44, the rear surface 36, or between any of the layers 20, 22, and 24. It should be understood that the any of the strips described herein may include the indicia 50.

Figure 6:
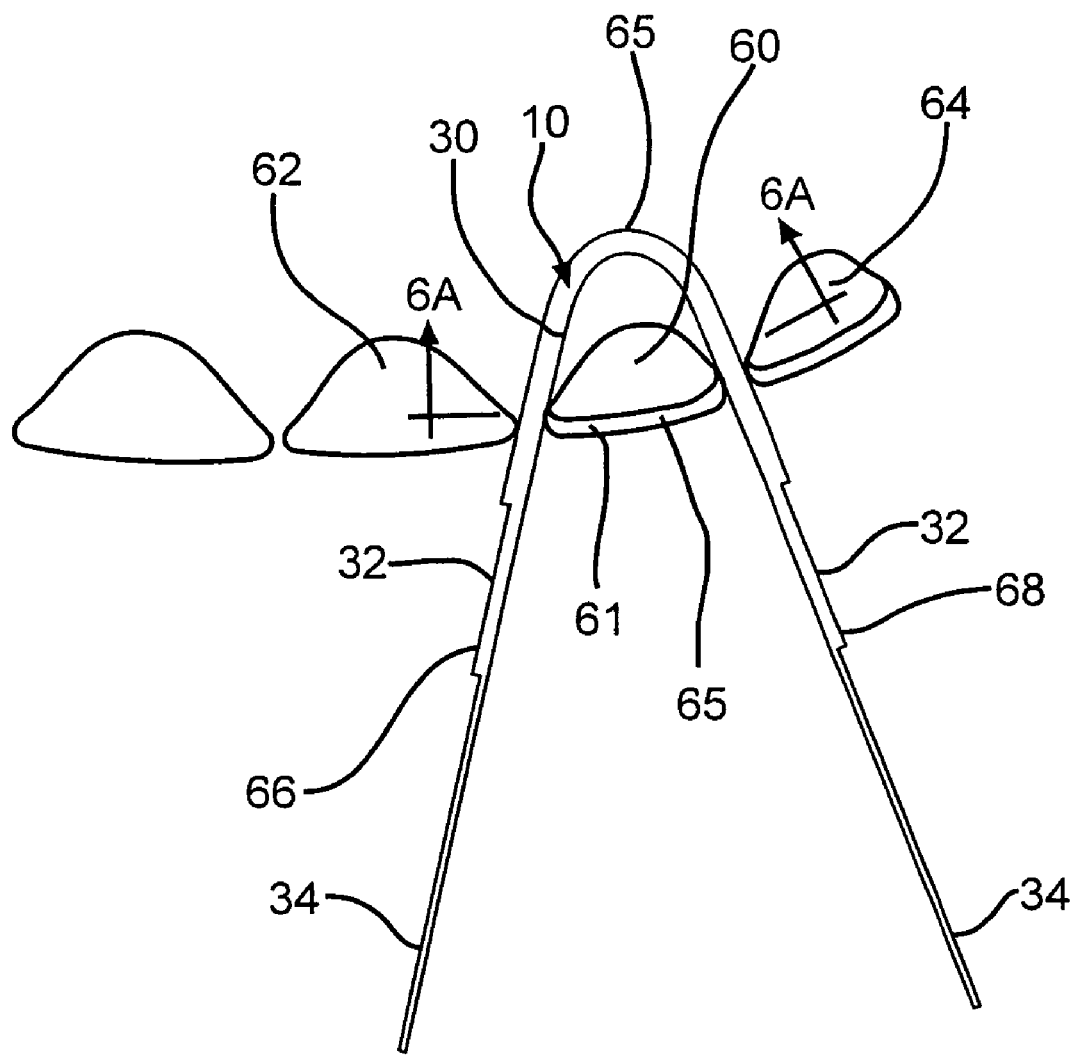
FIG. 6 is a schematic view of a portion of a patient's mouth depicting one method of use of the strip of FIG. 1.

Referring now to FIG. 6, one method of use of the strip 10 will now be explained in which the strip 10 is used for assisting in applying a dental material onto a tooth. More specifically, the strip 10 is used to isolate or shield a tooth 60 from adjacent teeth 62 and 64. The tooth 60 receives a veneer coating 61 on a facial surface 65 of the tooth 60.

A single strip 10 can be used to isolate both sides of the tooth 60 from each of the adjacent teeth 62 and 64 on either side of the tooth 60. Firstly, the strip 10 is preferably folded laterally across the width thereof at a fold 65. More preferably, the strip 10 is folded generally in half along the indicia 50 such that first and second half portions 66 and 68 are formed, thereby making the strip 10 more manageable within the mouth cavity and giving both half portions increased stability and rigidity. Thus, the fold 65 is formed in the strip 10 in the central portion 30. The end portion 34 of the first half portion 66 is inserted between the teeth 60 and 62. In many situations, the spacing between the teeth 60 and 62 is large enough that the thickness $t_3$ of the end portion 34 is not sufficient to frictionally secure the first half portion 66 between the teeth 60 and 62. In this circumstance, the first half portion 66 can be slid or pulled in a direction towards the facial side of the teeth (outward from the mouth) until the intermediate portion 32 is between the teeth 60 and 62. If the first half portion 66 still is not properly frictionally secured, the first half portion 66 can be pulled further until the central portion 30 is between the teeth 60 and 62. Thus, the strip 10 has three different thicknesses $t_1$, $t_2$, and $t_3$ in which to secure the strip 10 between the teeth 60 and 62. It should be understood that instead of using the first half portion 66 of the strip 10, a single strip similar to only half of the strip 10 may be used to isolate two adjacent teeth in a similar manner as described above.

Alternatively, if the spacing between the teeth 60 and 62 is relatively large, the strip 10 may be folded in half such that the first and second half portions 66 and 68 are adjacent to one another and both half portions 66 and 68 are simultaneously disposed between the teeth 60 and 62. Of course, the strip 10 can be folded over any suitable number of times to increase the total thickness.

Referring back to FIG. 6 and after having positioned the first half portion 66 between the teeth 60 and 62, to isolate the tooth 60 from the other adjacent tooth 64, the end portion 34 of the second half portion 68 is inserted between the teeth 60 and 64. Similarly, if the spacing between the teeth 60 and 64 is not sufficient to frictionally secure the second half portion 68 between the teeth 60 and 64, the second half portion 68 can be slid or pulled in a direction towards the facial side of the teeth until the intermediate portion 32 or the central portion 30 is between the teeth 60 and 64. FIG. 6 illustrates the strip 10 positioned such that the central portion 30 is disposed on either side of the tooth 60 between the adjacent teeth 62 and 64. The fold 65 is positioned in the lingual side of the teeth 60, 62, and 64.

Figure 3:
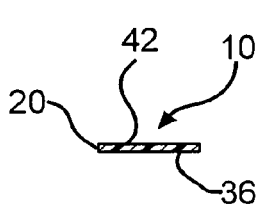
FIG. 3 is a cross-sectional view taken along lines 3-3 of FIG. 1.
Figure 4:
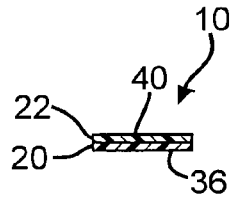
FIG. 4 is a cross-sectional view taken along lines 4-4 of FIG. 1.
Figure 5:
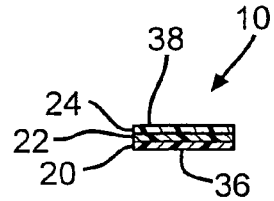
FIG. 5 is a cross-sectional view taken along 5-5 of FIG. 1.
Figure 6A:
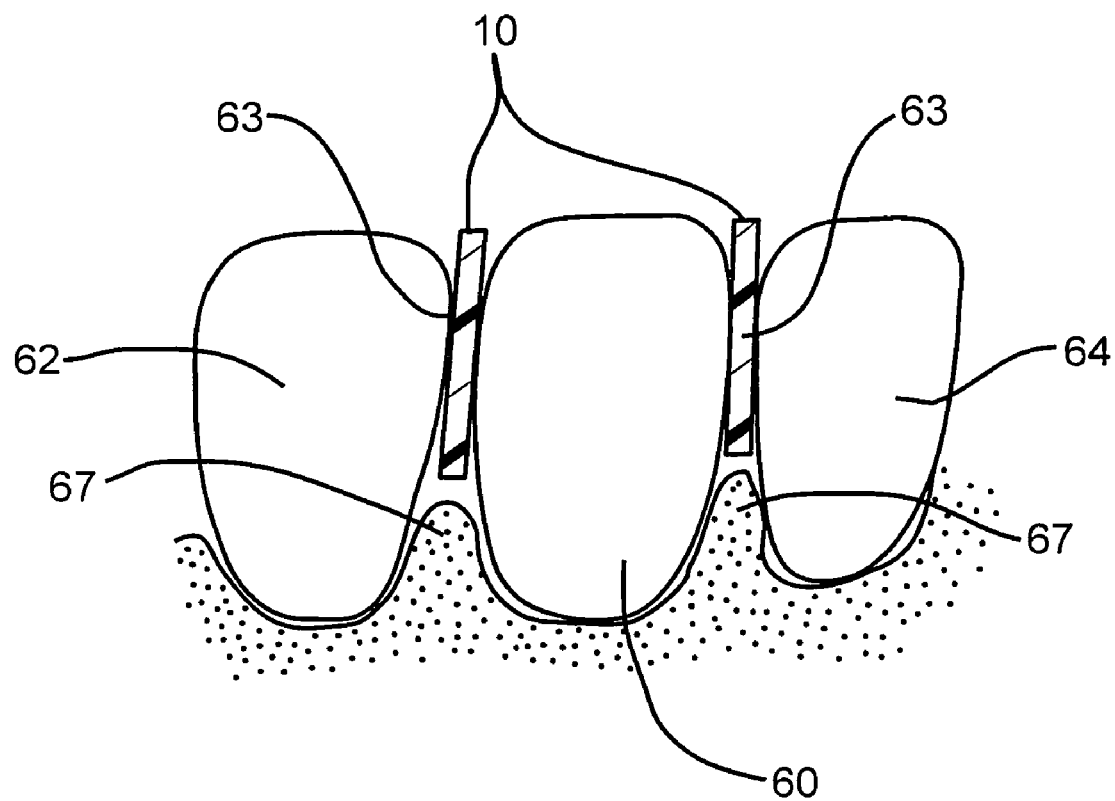
FIG. 6A is a schematic partial cross-sectional view taken along lines 6A-6A of FIG. 6.

Preferably, the strip 10 has a constant thickness across the lateral width W between the edges 12 and 14, as shown in FIGS. 3 through 5. As shown in FIG. 6A, the strip 10 contacts the teeth 60, 62, and 64 at contact points 63 which are above the gum line of gingival papilla 67. Preferably, the strip 10 is positioned such that lower portions of the strip 10 are positioned above the gum line of the gingival papilla, as shown in FIG. 6A. This has the advantage of causing less trauma to the gum tissue upon insertion between the teeth compared to other prior art strips having raised portions along their lateral width. Some prior art strips, such as those disclosed in U.S. Pat. Nos. 3,108,377; 6,619,956; and 3,795,052 have raised or tapered sections which are disposed in the sulcus of the gums contacting the gingival papilla and often times cause bleeding therein. The absence or reduction of bleeding should be minimized as much as possible especially if the strip 10 is used in a dental operation of applying dental material onto a tooth. Contrary to the prior art strips, the strip 10 is fictionally held in place at adjacent teeth contact points 63. This frictional attachment allows the strip 10 to be placed gingivally to the tooth contact point 63 and incisally to the interproximal papilla 67. This helps eliminate or reduce gingival bleeding compared to the prior art strips. However, it should be understood that the strip 10 may be disposed between the gingival papilla and the teeth if desired, such as for example, between the non-connecting portions of the gingival papilla 67 and the teeth. In such a case, the relative thinness of the strip 10 minimizes bleeding compared to prior art strips having raised portions. The relative thinness of the strip 10 also provides greater flexibility than the prior art strips having raised sections.

Once the strip 10 is properly positioned, the portions of the strip 10 extending towards the facial side of the teeth 60, 62, and 64 can be cut and removed. For example, the first and second half portions 66 and 68 can be cut about 5 mm beyond the surfaces of the teeth 60, 62, and 64. If desired, the strip 10 can be cut at the fold 65. However, it may be desirable to not cut the strip 10 and keep the fold 65 in tact to help improve the stability and rigidity of the strip 10 in the mouth.

The teeth 60, 62, and 64 are now isolated from one another by the strip 10 which helps prevent filling material, which is used to fill a cavity in one of the teeth 60, 62, and 64, from inadvertently being placed on an adjacent tooth. The strip 10 may also be used to aid in the forming of the filling material into the cavity preparation. The isolation of the teeth by the strip 10 is also particularly useful in dental procedures in which a veneer or coating 61 is placed on the facial side of the teeth. The strips 10 helps keep adjacent teeth from bonding together during the coating 61 placement. The coating 61 can be in the form of a paste which is sculpted and formed on the surface 65 of the tooth 60, or the coating 61 can be less viscous and be applied by brushing, spraying or applied by any suitable manner.

Prior to application of the dental coating 61, the tooth 60 is preferably prepared and cleaned prior to the insertion of the strip 10. The surface 65 of the tooth 60 is cleaned of any stains and deposits. After cleaning, the tooth 60 is preferably etched to promote bonding of the coating 61. The tooth 60 can be etched by any suitable manner, such as for example, by applying a chemical solution or gel to the surface 65 of the tooth. Application of a conventional phosphoric acid solution is a suitable etching technique. The etching generally roughens the surface 65 of the tooth 60 to form micro-projections to help mechanically anchor the flowable coating prior to polymerization. After etching the tooth surface, a primer, sealant, adhesive and/or bonding agent may be applied to the etched tooth surface for promoting the bonding of the subsequently applied coating 61. The etching solution and bonding agent may be applied to the surface 65 of the tooth 60 with a brush or other suitable instrument or device.

Alternatively, a self etching priming and bonding agent may be used in place of the separate etching solution and bonding agent described above. Essentially, the self etching priming bonding agent is a single component which is applied to the surface 65 of the tooth 60 and combines the steps of etching the tooth surface and applying a bonding agent for promotion of bonding the coating 61.

After proper tooth preparation, the coating 61 can then be applied. The strip 10 acts as a barrier so that if a flowable coating 61 is being applied to the surface 65 of the tooth 60, the flowable coating 61 will not flow onto the surface of the adjacent tooth 62 and 64. The strip 10 can also be used to help guide and form the interproximal margins of the coating 61 edges.

After application of the coating 61 onto the surface 65 of the tooth 60, the coating 61 is cured. A preferred curing process is light curing utilizing light curing initiators or photoinitiators in the coating mixture. During this curing process, the coating 61 undergoes a polymerization process to harden the coating 61. The coating 61 also exhibits color stability during the curing process. The brush application and curing process may be conducted tooth by tooth or by coating multiple teeth initially and then curing the teeth all together in one step.

Preferably, after the tooth 60 has been coated and cured, the strip 10 may be removed. The areas of the coating 61 which were adjacent the strip 10 may be finished, shaped, buffed, or polished with appropriate abrasive strips, or other interproximal finishing devices having varying grits. The facial surface of the coating 61 may also be finished with any suitable polishing device. Finishing is generally done to remove the oxygen inhibited layer on the surface of the coating 61 and results in a shine or aesthetically pleasing polished appearance.

The strip 10 can be used in a different manner than as described. For example, the entire strip 10 can be used to isolate one tooth from an adjacent tooth, wherein there is a relatively large gap. The strip 10 may be folded at the indicia 50, thereby doubling or increasing the thicknesses of the central portion 30, the intermediate portions 32, and the end portions 34. Alternatively, the strip 10 may be folded anywhere along its length to obtain a desired folded thickness.

Figure 7:
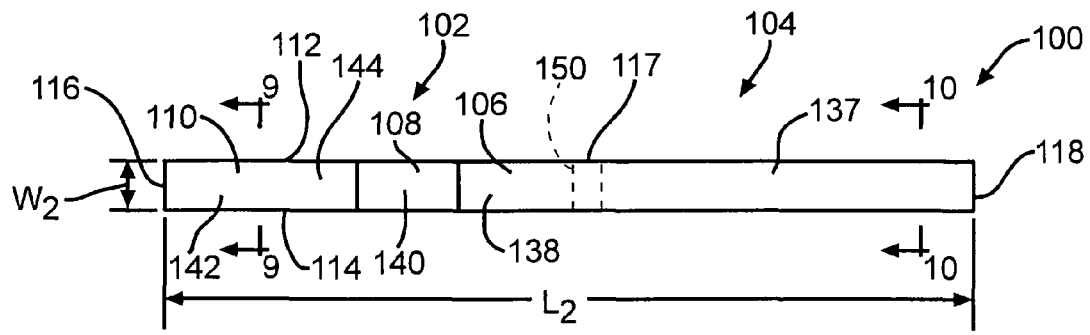
FIG. 7 is a plan view of a second embodiment of a dental strip.
Figure 8:
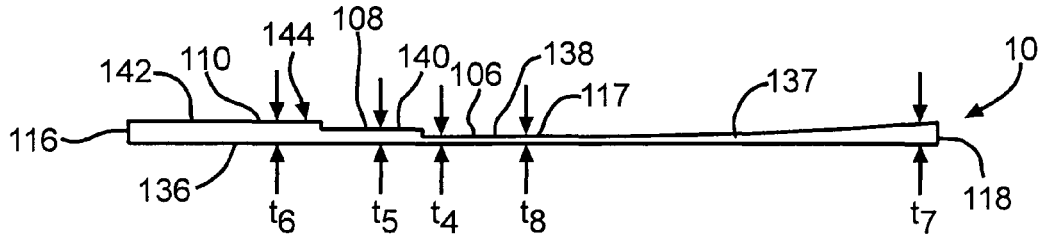
FIG. 8 is side elevational view of the strip of FIG. 7.
Figure 9:
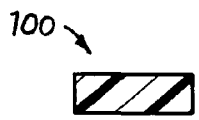
FIG. 9 is a cross-sectional view taken along lines 9-9 of FIG. 7.
Figure 10:
FIG. 10 is a cross-sectional view taken along lines 10-10 of FIG. 7.

There is illustrated in FIGS. 7 through 11 a second embodiment of a dental strip, indicated generally at 100, which may also be used in dental procedures for isolating or shielding the sides of adjacent teeth. The strip 100 defines a lateral width $W_2$ between edges 112 and 114. The strip 100 further defines a longitudinal length $L_2$ between ends 116 and 118. Preferably, the width $W_2$ of the strip 100 remains constant along the length of the strip 100, as best shown in FIG. 7. However, it should be understood that the width $W_2$ need not remain constant along the length.

The strip 100 is preferably made of a flexible material, such as plastic, such that it is easily manipulated within and exterior of a patient's mouth. The strip 100 may also be transparent to assist the dentist in viewing through the strip 100 during dental procedures and to facilitate light curing through the strip 100. Preferably, the strip 100 includes indicia 150 locating the approximate center of the length of the strip 100. Although the strip 100 is shown formed from a single piece not including individual multiple layers laminated together, it should be understood that the strip 100 could be formed as such.

The strip 100 includes a first half portion 102 and a second half portion 104 generally separated by the approximate center of the length of the strip 100. The first half portion 102 is stepped and includes a central portion 106, an intermediate portion 108, and an end portion 110. The intermediate portion 108 is disposed between the central portion 106 and the end portion 110. The central portion 106 has a thickness $t_4$ defined between a generally planar rear surface 136 and a generally planar surface 138. The intermediate portion 108 has a thickness $t_5$ defined between the rear surface 136 and a generally planar surface 140. The end portion 110 has a thickness $t_6$ defined between the rear surface 136 and a generally planar surface 142. The surfaces 138, 140, and 142 generally define a stepped front surface 144.

The second half portion 104 is generally tapered between the rear surface 136 and an outer tapered surface 137. The terms "taper", "tapered", and "tapers" herein refer generally to surfaces or portions which are not parallel with other corresponding surfaces or portions and can be either planar in shape or curved in shape. The second half portion 104 has an increasing thickness from a generally central portion 117 towards the end 118. Thus, a thickness $t_7$ at the end 118 of the strip 100 is greater than a thickness $t_8$ near the center portion 117. The tapered surface 137 can be essentially planar such that the thickness increases in a linear manner along the length of the strip 100. Alternatively, the tapered surface 137 can be curved such that the thickness increases nonlinearly along its length.

Although the first and second portions 102 and 104 are shown having essentially the same length, it should be understood that they may have any desired length relative to one another. Additionally, the lengths of the central portion 106, the intermediate portion 108, and the end portions 110 can be any desired size.

Figure 11:
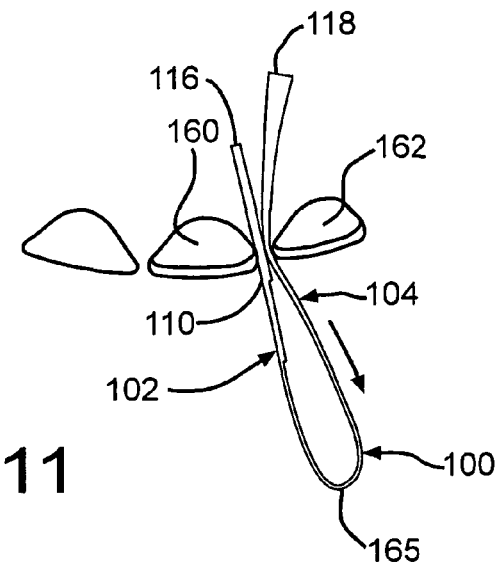
FIG. 11 is a schematic view of a portion of a patient's mouth depicting one method of use of the strip of FIG. 7.

Referring now to FIG. 11, one method of use of the strip 100 will now be explained in which the strip 100 is used for assisting in applying a dental material onto a tooth. More specifically, the strip 100 is used to isolate or shield a tooth 160 from an adjacent tooth 162.

The strip 100 is folded laterally across the width thereof at a fold 165 such as along the indicia 150 such that first and second half portions 102 and 104 are generally adjacent to one another. The central portions 106 and 117 of the first and second halves 102 and 104, respectfully, are simultaneously inserted between the teeth 160 and 162. The stepped first half portion 102 is slid or pulled in a direction towards the facial side of the teeth (outward from the mouth) until slight resistance is felt. The first half portion 102 may be pulled such that any one of the central portion 106, the intermediate portion 108, or the end portion 110 is adjacent the tooth 160. In FIG. 11, the end portion 110 is shown positioned adjacent the tooth 160. The second half portion 104 is then pulled in the same direction until the strip 100 is adequately frictionally secured between the teeth 160 and 162. The strip 100 can be pulled manually, or alternately, the strip 100 may be pulled with the assistance of a dental instrument, such as an explorer, by hooking the fold 165 and pulling. The sloped or tapered surface of the second half portion 104 provides a flared end which is relatively easy to grasp and pull.

The teeth 160 and 162 are now isolated from one another by the strip 100 which is particularly useful in dental procedures in which filling material is used to fill a cavity especially in a side portion of one of the teeth 160 and 162 which generally faces the other adjacent tooth 162 and 160. After the filing material has been placed in the tooth cavity, the strip 100 may be pulled against the filled tooth cavity to assist in forming the filling material to the shape of the tooth. The filling material can then be light cured through the transparent strip 100.

In an alternate method of use of the strip 100, only the second half portion 104 is inserted between the teeth 160 and 162. The tapered second half portion 104 is then pulled in the manner described above until the strip 100 is adequately frictionally secured between the teeth 160 and 162. This method has the advantage of being more flexible since a reduced thickness of the strip 100 is positioned near the teeth 160 and 162, thereby providing more flexibility to the strip 100 for forming the filling material to the shape of the tooth. Alternatively, the first half portion 102 of the strip 100 may just be inserted between the teeth 160 and 162 and pulled in the manner described above.

Any of the following embodiments of dental strips disclosed herein may be used in any suitable manner, such as those methods described above. All of the following strips illustrated in FIGS. 12 through 21 have portions along their length having different thicknesses, and it is preferred that the strips have a constant thickness across the lateral widths thereof. The strips are preferably made of transparent plastic, and may include indicia (not shown) for generally locating the center of the strips.

Figure 12:
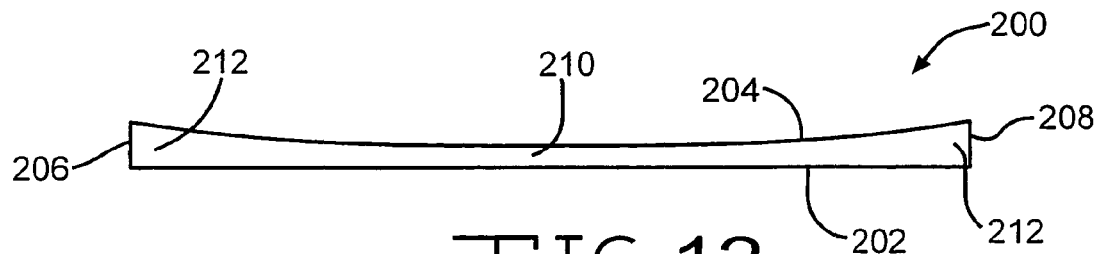
FIG. 12 is a side elevational view of a third embodiment of a dental strip, in accordance with the present invention.

There is illustrated in FIG. 12 a third embodiment of a dental strip, indicated generally at 200. The strip 200 includes a generally flat planar rear surface 202 and a front surface 204. The strip also includes ends 206 and 208. The strip has a generally thin central portion 210 and thicker end portions 212. The front surface 204 tapers upwardly from the central portion 210 towards both ends 206 and 208.

The strip 200 can be used to isolate adjacent teeth such that the strip 200 is generally folded in half at the central portion 210 which is then inserted between adjacent teeth. The strip 200 is then pulled at the fold such that the thickness of the strip 200 between the teeth increases as the strip 200 is pulled through between the teeth.

Figure 13:
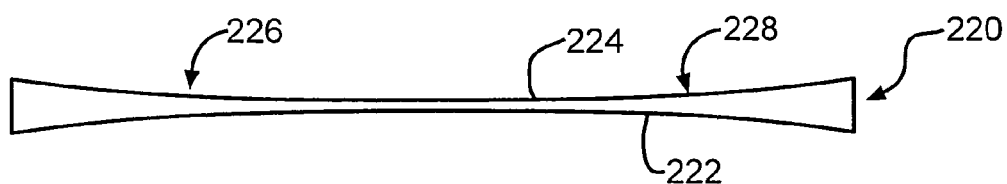
FIG. 13 is a side elevational view of a fourth embodiment of a dental strip, in accordance with the present invention.

There is illustrated in FIG. 13 a fourth embodiment of a dental strip, indicated generally at 220. The strip 220 is similar in function and structure as the strip 200 of FIG. 12 with an exception that the strip 220 has a rear surface 222 which is also tapered along with a tapered front surface 224. The taper on a first half portion 226 may be differently shaped from the taper on a second half portion 228, thereby creating different thickness of the strip 220 along the length of the first and second half portions 226 and 228 even though spaced equidistant from the center of the strip 220.

In an alternate embodiment of a strip (not shown), the strip may be tapered from one end continuously to the other end increasing in thickness such that the strip has a contour similar to the first or second half portions 226 and 228 of the strip 220. If desired, the strip 220 may be cut in half prior to use, thereby providing two single tapered strips. Alternatively, an alternate embodiment of a strip (not shown) in accordance with the present invention may be shaped as one of the first and second half portions of the illustrated strips herein.

Figure 14:
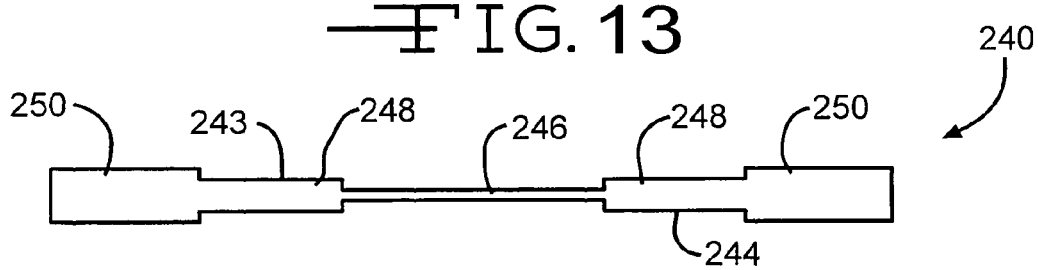
FIG. 14 is a side elevational view of a fifth embodiment of a dental strip, in accordance with the present invention.

There is illustrated in FIG. 14 a fifth embodiment of a dental strip, indicated generally at 240. The strip 240 also includes a stepped front surface 243 and a stepped rear surface 244. The strip 240 includes a central portion 246, a pair of intermediate portions 248, and a pair of end portions 250. Each of the intermediate portions 248 are disposed between a respective end portion 250 and the central portion 246. The end portions 250 have the largest thickness, with the intermediate portions 248 and central portion 246 reducing in thickness, consecutively towards the center of the length of the strip 240.

The strip 240 can be used to isolate adjacent teeth such that the strip 240 is generally folded in half at the central portion 246 which is then inserted between adjacent teeth. The strip 240 is then pulled at the fold such that the thickness of the strip 240 between the teeth increases as the strip 240 is pulled through between the teeth.

Figure 15:
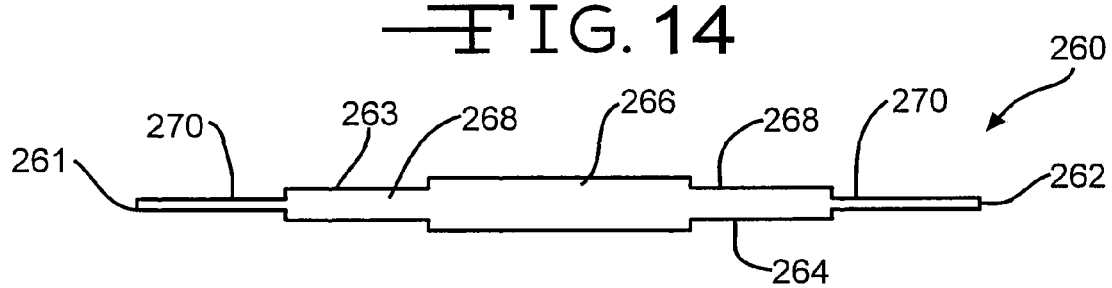
FIG. 15 is a side elevational view of a sixth embodiment of a dental strip, in accordance with the present invention.

There is illustrated in FIG. 15 a sixth embodiment of a dental strip, indicated generally at 260. The strip 260 defines ends 261 and 262. The strip 260 also includes a stepped front surface 263 and a stepped rear surface 264. The strip 260 includes a central portion 266, a pair of intermediate portions 268, and a pair of end portions 270. Each of the intermediate portions 268 are disposed between a respective end portion 270 and the central portion 266. The central portion 266 has the largest thickness, with the intermediate portions 268 and end portions 270 reducing in thickness, consecutively towards the respective ends 261 and 262 of the strip 260.

The strip 260 can be used to isolate adjacent teeth such that the strip 260 is generally folded in half at the central portion 266. The adjacent end portions 270 are then inserted between adjacent teeth. The strip 260 is then pulled at the ends 261 and 262 such that the thickness of the strip 260 between the teeth increases as the strip 260 is pulled through between the teeth.

Figure 16:
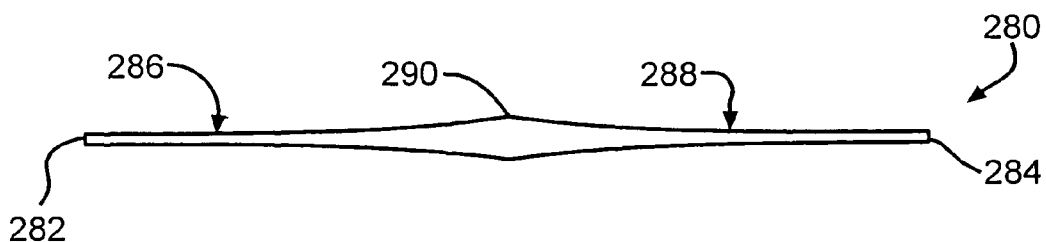
FIG. 16 is a side elevational view of a seventh embodiment of a dental strip, in accordance with the present invention.

There is illustrated in FIG. 16 a seventh embodiment of a dental strip, indicated generally at 280. The strip 280 had ends 282 and 284. The strip 280 further includes a first half portion 286 and a second half portion 288 which are generally separated at a center point 290 of the length of the strip 280. The thickness of the strip 280 is greatest at the center point 290. The first and second half portions 286 and 288 taper in reduced thickness from the center point 290 to the ends 282 and 284.

The strip 280 can be used to isolate adjacent teeth such that the strip 280 is generally folded in half at the center point 290. The portions of the strip 280 near the ends 282 and 284 are then inserted between adjacent teeth. The strip 280 is then pulled at the ends 282 and 284 such that the thickness of the strip 280 between the teeth increases as the strip 280 is pulled through between the teeth.

Figure 17:
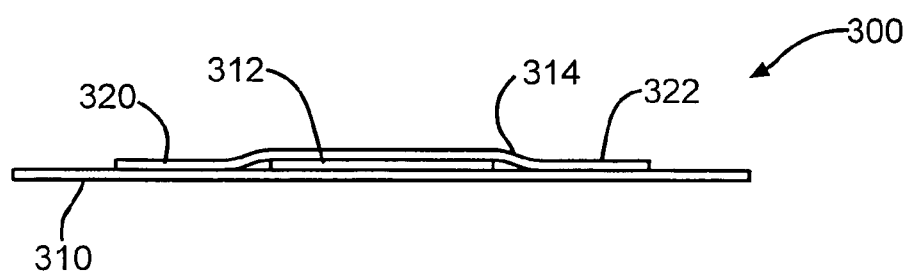
FIG. 17 is a side elevational view of an eighth embodiment of a dental strip, in accordance with the present invention.

There is illustrated in FIG. 17 an eighth embodiment of a dental strip, indicated generally at 300. The strip 300 is similar in function and overall shape to the strip 10 of FIGS. 1 through 6, but is formed in a different manner. The strip 300 includes three layers; a base layer 310, a covered layer 312, and an outer layer 314. The covered layer 312 is disposed between the base layer 310 and the outer layer 314. The covered layer 312 is shorter in length than the outer layer 314 such that the outer layer 314 includes end portions 320 and 322 which extend longitudinally beyond the ends of the covered layer 312. The layers 310, 312, and 314 are preferably separate strips laminated together to form the strip 300. The separate layers 310, 312, and 314 may be laminated together by any suitable manner, such as by an adhesive, ultrasonic welding or other welding techniques. Alternatively, the layers 310, 312, and 314 may be subjected to heat to melt adjacent surfaces, thereby laminating the layers 310, 312, and 314 together.

Figure 18:
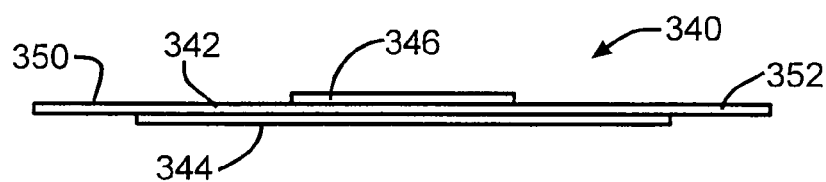
FIG. 18 is a side elevational view of an ninth embodiment of a dental strip, in accordance with the present invention.

There is illustrated in FIG. 18 a ninth embodiment of a dental strip, indicated generally at 340. The strip 340 is similar in function and overall shape to the strip 10 of FIGS. 1-6 and the strip 300 in FIG. 17, but is formed in a different manner. The strip 340 includes three layers; a base layer 342, a lower layer 344, and an upper layer 346. The layers 342, 344, and 346 are centrally aligned with one another and the base layer 342 is disposed between the layers 344 and 346. The upper layer 346 is shorter in length than the base layer 342 and the lower layer 344. The lower layer 344 is shorter in length than the base layer 342 such that the outer layer base layer 342 includes end portions 350 and 352 which extend longitudinally beyond the ends of the lower layer 344. The layers 342, 344, and 346 are preferably separate strips laminated together to form the strip 340. The separate layers 342, 344, and 346 may be laminated together by any suitable manner, such as by an adhesive, ultrasonic welding or other welding techniques. Alternatively, the layers 342, 344, and 346 may be subjected to heat to melt adjacent surfaces, thereby laminating the layers 342, 344, and 346 together.

The strips 260, 280, 300, and 340 of FIGS. 15 through 18 generally include end portions having a thickness which is less than the central portion. In use, the strips 260, 280, 300, and 340 can be inserted between adjacent teeth such that the strips are folded preferably in half and the thinner end portions are placed between adjacent teeth. One or both of the end portions can be pulled or slid between the teeth such that the thickness of the strips 260, 280, 300, and 340 between the teeth increases. The end portion or portions are pulled until the strips 260, 280, 300, and 340 are adequately frictionally secured between the teeth.

Figure 19:
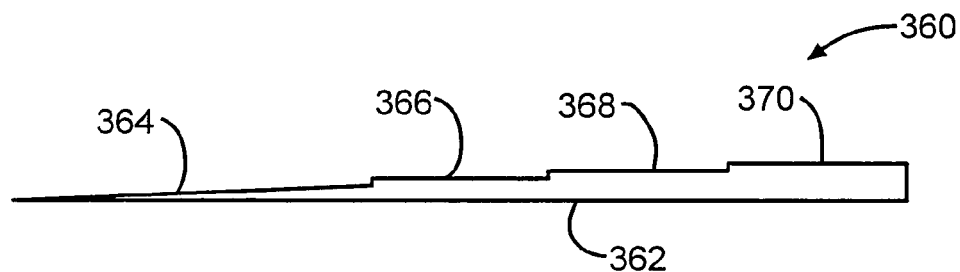
FIG. 19 is a side elevational view of a tenth embodiment of a dental strip, in accordance with the present invention.

There is illustrated in FIG. 19 a tenth embodiment of a dental strip, indicated generally at 360. The strip 360 is formed of a combination of tapered and stepped portions. The strip 360 includes a generally flat planar rear surface 362. The strip 360 further includes a generally tapered surface 364 and a plurality of stepped surfaces 366, 368, and 370 defining a sequentially increasing thickness of the strip 360. The tapered surface 364 may be curved or planar. In a preferred embodiment, the surfaces 366, 368, and 370 are generally parallel with the rear surface 362.

Figure 20:
FIG. 20 is a side elevational view of an eleventh embodiment of a dental strip, in accordance with the present invention.

There is illustrated in FIG. 20 an eleventh embodiment of a dental strip, indicated generally at 380. The strip 380 is formed of a combination of tapered and stepped portions. The strip 380 includes a generally flat planar rear surface 382. The strip 380 further includes a pair of stepped surfaces 384 and 386 and a tapered surface 388. The strip 380 increases in thickness from a first end 390 to a second end 392.

Figure 21:
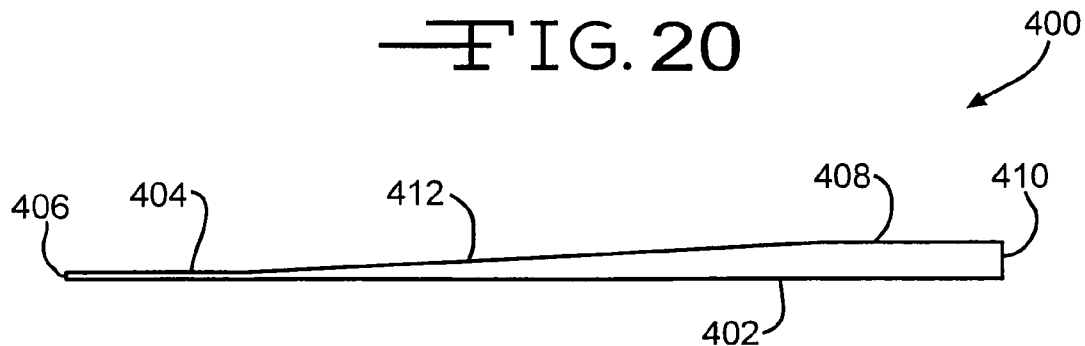
FIG. 21 is a side elevational view of a twelfth embodiment of a dental strip, in accordance with the present invention.

There is illustrated in FIG. 21 a twelfth embodiment of a dental strip, indicated generally at 400. The strip 400 is formed of a combination of tapered and stepped portions. The strip 400 includes a generally flat planar rear surface 402. The strip 402 further includes a generally flat first surface 404 parallel with the rear surface 402 on a first end 406 of the strip 400. A generally flat second surface 408 is parallel with the rear surface 402 on a second end 410 of the strip 400. A tapered surface 412 is between the first and second surfaces 404 and 408. The strip 400 increases in thickness from the first end 406 to the second end 410.

It should be understood that the dental strip of the present invention can include any number or types of features shown and described with respect to the strips shown in the figures herein. It should also be understood that all of the strips shown and described herein can be cut in half, preferably generally around the mid-point, and either half may then be used alone to accomplish its function as described above.

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

What is claimed is:

1. A dental strip for isolating respective sides of adjacent teeth from one another, the dental strip comprising:
    a base layer formed from a flexible material having a top surface and a rear surface, first and second ends that define a length therebetween, and first and second edges that define a width therebetween, wherein the length of the base layer is substantially greater than the width of the base layer;
    an intermediate layer formed from a flexible material having a top surface and a rear surface, first and second ends that define a length therebetween, and first and second edges that define a width therebetween, wherein the length of the intermediate layer is less than the length of the base layer, and wherein the rear surface of the intermediate layer engages the top surface of the base layer such that first and second portions of the top surface of the base layer respectively adjacent to the first and second ends thereof are exposed, wherein the width of the intermediate layer is the same as the width of the base layer; and
    a top layer formed from a flexible material having a top surface and a rear surface, first and second ends that define a length therebetween, and first and second edges that define a width therebetween, wherein the length of the top layer is less than the length of the intermediate layer, and wherein the rear surface of the top layer engages the top surface of the intermediate layer such that first and second portions of the top surface of the intermediate layer respectively adjacent to the first and second ends thereof are exposed;

wherein the base layer defines a base layer thickness, the intermediate layer defines an intermediate layer thickness, and the top layer defines a top layer thickness, and wherein each of the base layer thickness, the intermediate layer thickness, and the top layer thickness are generally equal and are constant across the widths thereof.

2. The dental strip defined in claim 1 wherein the base layer, the intermediate layer, and the top layer are formed from separate pieces of material that are laminated together.

3. The dental strip defined in claim 1 wherein the base layer, the intermediate layer, and the top layer are formed from a single piece of material.

* * * * *